Oct. 15, 1974 D. W. McKENZIE Plant Pat. 3,637
APPLE TREE
Filed Aug. 1, 1973
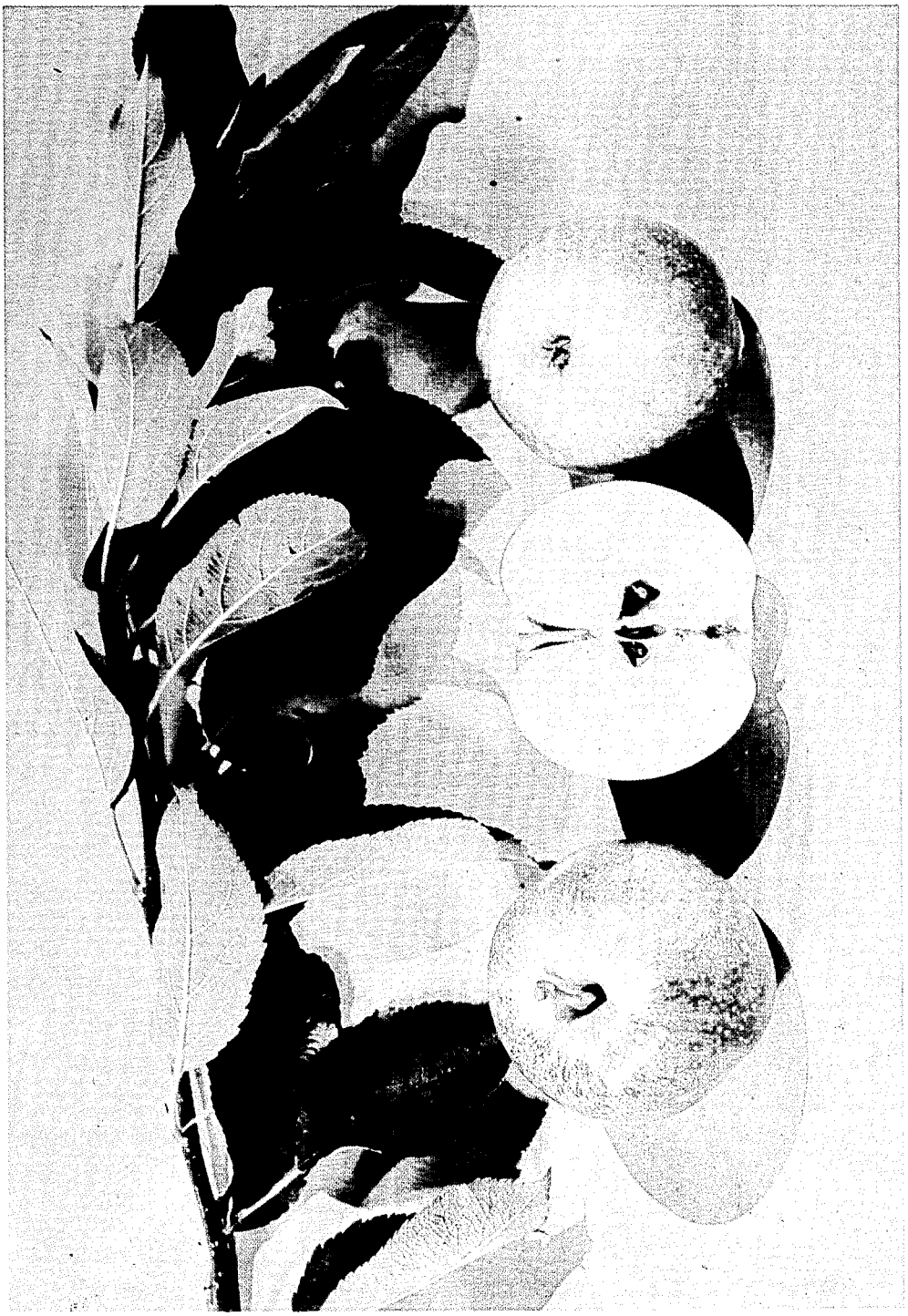

United States Patent Office

Plant Pat. 3,637
Patented Oct. 15, 1974

3,637
APPLE TREE

Donald W. McKenzie, Havelock North, New Zealand, assignor to Stark Bro's Nurseries & Orchards Co., Louisiana, Mo.

Filed Aug. 1, 1973, Ser. No. 384,616
Int. Cl. A01h *5/03*
U.S. Cl. Plt.—34 1 Claim

The present invention relates to a new and distinct variety of apple tree which was discovered by me among a block of seedlings derived from crossing the apple varieties known as "Kidd's Orange" (an unpatented New Zealand apple variety) and "Golden Delicious" (unpatented), and which were being grown and tested under my direction and control in the fruit research orchard of my assignee located at Havelock, New Zealand.

As the result of my tests aforesaid, I recognized and selected this new seedling as being a new and improved apple variety which is distinguished from its parents, as well as from all other apple varieties and possessed of unusual and commercially desirable features, as evidenced by the following unique combination of characteristics which are particularly outstanding in the new variety:

(1) A combination of some of the best characteristics of both parent varieties, along with features which are superior to other late summer apples;
(2) The production of fruit having excellent texture and flavor, said flavor being mildly subacid and somewhat similar to but sweeter than that of "Cox Orange" fruit;
(3) A fruit form similar to that of "Golden Delicious," but somewhat smaller in size;
(4) A distinctive and attractive golden yellow fruit color, with an attractive bright red blush;
(5) A late summer fruit maturing season which is about the same as "Cox Orange" grown in the mid-western section of the United States, and about two weeks earlier than the variety "Jonathan" (unpatented);
(6) An ability of the fruit to hang on the tree until fully colored and ripe without premature dropping; and
(7) Good keeping qualities of the fruit.

Asexual reproduction of the new variety as performed by me by budding in New Zealand, and also performed by a succeeding assignee at Louisiana, Mo., U.S.A., shows that the foregoing characteristics and distinctions come true and are established and transmitted through succeeding propagations.

The accompanying drawing shows typical specimens of the foliage and fruit of the new applie variety, with one of the fruit specimens being shown in cross-section, and all as depicted in color.

The following is a detailed description of the new apple variety, with color terminology in accordance with Ridgway's Color Standards and Nomenclature [hereinafter abbreviated as (R)] and the Munsell Color Chart [hereinafter abbreviated as (M)], except where general color terms of ordinary dictionary significance are obvious:

Parentage: A cross of "Kidd's Orange" and "Golden Delicious" apple varieties.
Locality where grown and observed: Louisiana, Mo., U.S.A.
Dates of first and last pickings: About Aug. 25 and Sept. 5, respectively.
Tree: Medium small; vigorous; spreading; low; round-topped; medium slow growing; hardy; productive; regular bearer.
*Trunk*—Medium stockiness; smooth.
*Branches* — Medium thickness; smooth; much-branched. Color—Dresden Brown, Plate XV, Color No. 17′, tone *k* (R). Lenticles—Numerous; medium large.

Leaves: Medium large; medium wide; medium long; oval; abruptly pointed; medium thickness; smooth.
*Length*—From about 4 inches to 4½ inches.
*Width*—From about 1⅞ inches to 2⅛ inches.
*Color*—Moderate Olive Green, Hue 7.5 GY 4/4 (M).
*Margin*—Crenate; finely serrate.
*Petiole*—Long (from about 1⅜ inch to 1½ inch); medium slender.
Flowers: Medium early.
*Dates of first and full bloom*—About Apr. 18 and Apr. 30, respectively.
*Size*—Medium small.
*Color*—White.
Fruit:
*Maturity when described*—Eating ripe.
*Size*—Uniform. Axial diameter—About 2½ inches. Transverse diameter—From about 2½ inches to 2¾ inches.
*Form*—Globose.
*Cavity*—Symmetrical; abrupt at base; apex acuminate. Depth—About ⅞ inch. Breadth—About 1 inch. Markings—Russet—Old Gold, Plate XVI, Color No. 19′, tone *i* (R).
*Basin*—Symmetrical; rounded; wide; undulate; pubescent. Depth—About 5/16 inch. Breadth—About ¾ inch. Markings—None.
*Stem*—Medium stout. Length—About ⅞ inch. Breadth—About 3/32 inch.
*Calyx*—Closed; persistent; broadly lanceolate; about ¼ inch long; approximate; reflexed from base at apex; converged from base toward center; both outer and inner surfaces pubescent.
*Skin*—Thin; tough; smooth; glossy; waxed. Dots—Conspicuous; many; small; even; ruptured; circular; color of dots—Straw-Yellow, Plate XVI, Color No. 21′, tone *d* (R). Ground color—Straw-Yellow, Plate XVI, Color No. 21′, tone *d* (R). Color markings—Rose Doree, Plate I, Color No. 3, tone *b* (R). Bloom—Wanting. Scarskin—Very Light; color—White. General color effect—Bright light red over cream colored ground.
*Flesh*—Juicy.
*Color*—Satiny white, with yellowish tint.
*Texture*—Firm; tender; fine; crisp.
*Flavor*—Subacid; sprightly; rich.
*Aroma*—Distinct.
*Quality*—Best.
*Core*—Median. Bundle area—Medium small; oblate; symmetrical. Halves of area—Equal. Bundles—Inconspicuous; in one whorl. Core lines—Clasping. Cross section—Indistinct. Carpellary area—Indistinct. Calyx tube—Glabrous toward base, funnel-form; stem of funnel—long; depth of tube to shoulder—about 3/16 inch. Entire depth—about ½ inch. Styles—Present; united toward base; glabrous at base to point of branching. Stamens—In one distinct whorl; median. Auxiliary cavity—Present. Seed cells—Axile; open; cell walls—distant; thin; tough; length—about 9/16 inch; breadth—about ⅜ inch. Longitudinal section—Orbicular; obtuse at apex. Surface—Fissured; smooth. Cross section—Broad.
Seeds: From 8 to 10 in number and all perfect; no more than 2 per cell.
*Length*—About 5/16 inch.
*Breath*—About 3/16 inch.
*Form*—Obtuse.
*Color*—Burnt Umber, Plate XXVIII, Color No. 9″, tone *m* (R).
Use: Market, dessert.

Keeping quality: Good; about 60 days in ordinary storage.

I claim:

1. A new and distinct variety of apple tree, substantially as herein shown and described, characterized particularly as to novelty by the unique combination of a combination of some of the best characteristics of both parent varieties, along with features which are superior to other late summer apples, the production of fruit having excellent texture and flavor, said flavor being mildly subacid and somewhat similar to but sweeter than that of "Cox Orange" fruit, a fruit form similar to that of "Golden Delicious," but somewhat smaller in size, a distinctive and attractive golden yellow fruit color, with an attractive bright red blush, a late summer fruit maturing season which is about the same as "Cox Orange" grown in the mid-western section of the United States, and about two weeks earlier than the variety "Jonathan" (unpatented), an ability of the fruit to hang on the tree until fully colored and ripe without premature dropping, and good keeping qualities of the fruit.

No references cited.

ROBERT E. BAGWILL, Primary Examiner

UNITED STATES PATENT AND TRADEMARK OFFICE

CERTIFICATE OF CORRECTION

PATENT NO. : Plant Patent No. 3,637

DATED : October 15, 1974

INVENTOR(S) : Donald W. McKenzie

It is certified that error appears in the above-identified patent and that said Letters Patent is hereby corrected as shown below:

On the title page,
Delete the present title and insert -- APPLE TREE - KIDD'S D-8 VARIETY --.

Col. 1, at the end of line 47, insert -- The new variety has been named the Kidd's D-8 variety --.

Signed and Sealed this

*Twenty-sixth* Day of *March 1985*

[SEAL]

*Attest:*

DONALD J. QUIGG

*Attesting Officer* *Acting Commissioner of Patents and Trademarks*